United States Patent [19]

Tobe et al.

[11] Patent Number: 4,814,507

[45] Date of Patent: * Mar. 21, 1989

[54] ARYLSULFONE COMPOUNDS AS ANTI-ULCER AGENTS

[75] Inventors: Akihiro Tobe; Shinichiro Fujimori; Tomoshi Yamazaki; Mamoru Sugano, all of Kanagawa; Ryoji Kikumoto; Issei Nitta, both of Tokyo, all of Japan

[73] Assignee: Mitsubishi Chemical Industries, Limited, Tokyo, Japan

[*] Notice: The portion of the term of this patent subsequent to Mar. 29, 2005 has been disclaimed.

[21] Appl. No.: 95,766

[22] Filed: Sep. 14, 1987

Related U.S. Application Data

[63] Continuation of Ser. No. 838,569, Mar. 11, 1986, Pat. No. 4,734,500.

[30] Foreign Application Priority Data

Mar. 14, 1985 [JP] Japan .................................. 60-51202

[51] Int. Cl.⁴ ..................... C07C 87/28; C07C 147/00
[52] U.S. Cl. ...................................... 564/336; 544/392; 544/394; 544/398; 544/403; 564/280; 564/304; 564/347; 564/374; 564/384; 568/30
[58] Field of Search ............... 544/392, 394, 398, 403; 564/336, 280, 304, 347, 374, 384; 568/30

[56] References Cited

U.S. PATENT DOCUMENTS 4,734,500 3/1988 Tobe et al. ...................... 544/398

OTHER PUBLICATIONS

Kikumoto et al, CA 94–57950e (1981).
Kikumoto et al, CA 99–175384z (1983).
Jaachim et al, CA 104–168125j (1986).
Kikumoto et al, J. Med. Chem. 1981, 24(2), 145–8.

*Primary Examiner*—Donald G. Daus
*Assistant Examiner*—Cecilia Shen
*Attorney, Agent, or Firm*—Oblon, Fisher, Spivak, McClelland & Maier

[57] ABSTRACT

A novel sulfone compound represented by the general formula (I)

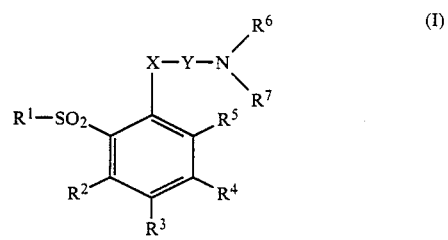

wherein $R^1$ is cyclohexyl, phenyl; or a phenyl substituted with a group selected from nitro, $C_1$–$C_3$ alkyl, $C_1$–$C_3$ alkoxy and halogen; $R^2$, $R^3$, $R^4$ and $R^5$ are respectively hydrogen, halogen, cyano or carbonyl, wherein $R^1$ and $R^2$ may form an o-phenylene or an o-phenylene substituted with at least one group selected from nitro $C_1$–$C_3$ alkyl, $C_1$–$C_3$ alkoxy and halogen; X is oxygen or methylkene; Y is -$(CH_2)_n$—, wherein n is an integer of 0, 5 or 6, or

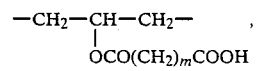

wherein m is an integer 1–3; $R^6$ is hydrogen, $C_1$–$C_3$ alkyl, ω-alkylaminoalkyl, wherein each alkyl has 1–3 carbon atoms, or ω-dialkylaminoalkyl, wherein each alkyl has 1–3 carbon atoms; $R^7$ is hydrogen or $C_1$–$C_3$ alkyl; and $R^6$ and $R^7$ may form a ring together with N, or

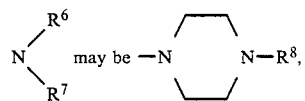

wherein $R^8$ is hydrogen, $C_1$–$C_3$ hydroxyalkyl or phenyl; or a pharmaceutically acceptable salt thereof is disclosed. The compound has anti-ulcer effect.

2 Claims, No Drawings

ARYLSULFONE COMPOUNDS AS ANTI-ULCER AGENTS

This is a continuation, of application Ser. No. 06/838,569, filed Mar. 11, 1986, now U.S. Pat. No. 4,734,500.

FIELD OF THE INVENTION

This invention relates to a class of novel arylsulfone compounds. The arylsulfone compounds of this invention and the pharmaceutically acceptable addition salts thereof have excellent anti-ulcer effect.

BACKGROUND OF THE INVENTION

Various compounds have hitherto been proposed as anti-ulcer agents. Inter alia, cimetidine, which is a histamine $H_2$-receptor blocker, is widely used because of excellent anti-ulcer effect. However, some misgivings have been pointed out with respect to several problems encountered with cimetidine. (Refer to NIKKEI MEDICAL, May 14, 1984, p. 26–34.)

We have made an extensive study in search of compounds which have chemical structures entirely different from those which have been proposed so far and have excellent anti-ulcer activity, and have found that 1-[4-(methylamino)-butoxy]-2-(phenylsulfonyl)benzene (Journal of Medical Chemistry, Vol. 24, No. 2, 145–148 (1981)) and related compounds have unexpected anti-ulcer activity, and upon extending our study to further encompass different compounds we attained this invention.

DISCLOSURE OF THE INVENTION

The present invention provides an arylsulfone compound represented by the general formula (I)

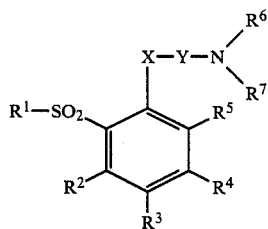
(I)

wherein $R^1$ is cyclohexyl; phenyl; or a phenyl group substituted with a group selected from nitro, $C_1$–$C_3$ alkyl, $C_1$–$C_3$ alkoxy groups and a halogen atom; $R^2$, $R_3$, $R^4$ and $R^5$ are respectively a hydrogen atom, a halogen atom, cyano or carboxyl, wherein $R^1$ and $R^2$ may form an o-phenylene group or an o-phenylene group substituted with at least one group selected from nitro, $C_1$–$C_3$ alkyl, $C_1$–$C_3$ alkoxy groups and a halogen atom; X is an oxygen atom or a methylene group; Y is —$(CH_2)_n$—, wherein n is an integer of 0 or 5 or 6, or

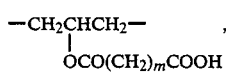

wherein m is an integer of 1–3; $R^6$ is a hydrogen atom, a $C_1$–$C_3$ alkyl, ω-alkylaminoalkyl group, wherein each alkyl has 1–3 carbon atoms or ω-dialkylaminoalkyl, wherein each alkyl has 1–3 carbon atoms; $R^7$ is a hydrogen atom or a $C_1$–$C_3$ alkyl group, and $R^6$ and $R^7$ may form a ring together with N, or

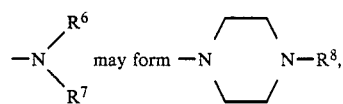

wherein $R^8$ is a hydrogen atom, a $C_1$–$C_3$ alkyl, $C_1$–$C_3$ hydroxyalkyl or phenyl group; and a pharmaceutically acceptable salt thereof.

Preferred compounds of this invention are those of general formula (I) wherein $R^1$ is cyclohexyl; phenyl; or a phenyl substituted with at least one group selected from nitro, $C_1$–$C_3$ alkyl such as methyl, ethyl or propyl, etc., $C_1$–$C_3$ alkoxy such as methoxy, ethoxy, etc. and a halogen atom such as chlorine, bromine, etc.; $R^2$ is a hydrogen atom or forms an o-phenylene group together with $R^1$; $R^3$ is a hydrogen atom; a halogen atom such as chlorine, bromine, etc.; cyano or carboxyl; $R^4$ is hydrogen atom or halogen atom such as chlorine, bromine, etc.; $R^5$ is hydrogen atom; X is oxygen or methylene group; Y is —$(CH_2)_n$—, wherein n is an integer of 0, 5 or 6, or

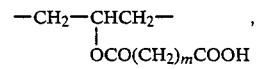

wherein m is an integer of 1–3; $R^6$ is a hydrogen atom, $C_1$–$C_3$ alkyl such as methyl, ethyl, etc.; the ω-alkylaminoalkyl, wherein each alkyl has 1–3 carbon atoms, such as methylaminoethyl; or ω-dialkylaminoalkyl, wherein each alkyl has 1–3 carbon atoms, such as diethylaminoethyl, dimethylaminoethyl, etc.; $R^7$ is a hydrogen atom or $C_1$–$C_3$ alkyl such as methyl, ethyl, etc.; and $R^6$ and $R^7$ may form

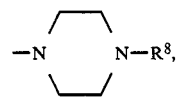

wherein $R^8$ is a hydrogen atom, $C_1$–$C_3$ alkyl such as methyl, ethyl, etc., $C_1$–$C_3$ hydroxylalkyl such as 2-hydroxyethyl, etc.

More preferred compounds of this invention are those of general formula (I) wherein $R^1$ is cyclohexyl; phenyl; a phenyl substituted with nitro or methyl; $R^2$ is a hydrogen atom or forms an o-phenylene group together with $R^1$; $R^3$ is a hydrogen atom, a bromine atom or carboxyl; $R^4$ and $R^5$ are respectively a hydrogen atom; X is an oxygen atom; Y is —$(CH_2)_n$—, wherein n is 0, 5 or 6, or

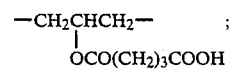

$R^6$ is a hydrogen atom, methyl, dimethylaminoethyl or methylaminoethyl; $R^7$ is a hydrogen atom or methyl, and

may be 4-methyl-1-piperazinyl.

Examples of the most preferred compounds of this invention are as follows:

5-[2-(phenylsulfonyl)phenoxy]-N-methylpentylamine
5-[2-(phenylsulfonyl)phenoxy]-N,N-dimethylpentylamine
6-[2-(phenylsulfonyl)phenoxy]-N-methylhexylamine
6-[2-(phenylsulfonyl)phenoxy]-N,N-dimethylhexylamine
5-[2-(2-methylphenylsulfonyl)phenoxy]-N-methylpentylamine
5-[2-(2-methylphenylsulfonyl)phenoxy]-N,N-dimethylpentylamine
5-[2-(2-nitrophenylsulfonyl)phenoxy]-N-methylpentylamine
5-[2-(4-nitrophenylsulfonyl)phenoxy]-N-methylpentylamine
5-[4-bromo-2-(phenylsulfonyl)phenoxy]-N-methylpentylamine
5-[4-carboxy-2-(phenylsulfonyl)phenoxy]-N-methylpentylamine
2-(3-carboxypropionyloxy)-3-[2-(phenylsulfonyl)phenoxy]-N,N-dimethylpropylamine
5-[2-(cyclohexylsulfonyl)phenoxy]-N-methylpentylamine
5-[2-(cyclohexylsulfonyl)phenoxy]-N,N-dimethylpentylamine
N-[2-(phenylsulfonyl)benzyl]-N-methylamine
N'-[2-(phenylsulfonyl)benzyl]-N,N-dimethylethylenediamine
N'-methyl-N'-[2-(phenylsulfonyl)benzyl]-N-methylethylenediamine
1-[2-(phenylsulfonyl)benzyl]-4-methylpiperazine
4-(5-dimethylaminopentyloxy)dibenzothiophene-5,5'-dioxide Acid addition salts of the above arylsulfone compounds are included in the scope of this invention.

Examples of such acid addition salts are hydrochloric acid salt, hydrobromic acid salt, sulfuric acid salt, phosphoric acid salt, nitric acid salt, acetic acid salt, succinic acid salt, adipic acid salt, propionic acid salt, tartaric acid salt, maleic acid salt, citric acid salt, benzoic acid salt, toluenesulfonic acid salt, methanesulfonic acid salt, etc.

The processes for preparation of the compounds of this invention will now be explained.

The arylsulfone compounds of this invention represented by the general formula (IV) are obtained by reacting an ω-halogenoalkoxy derivative of the general formula (II) with an amine of the general formula (III)

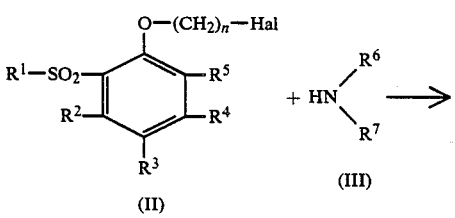

(II)

(III)

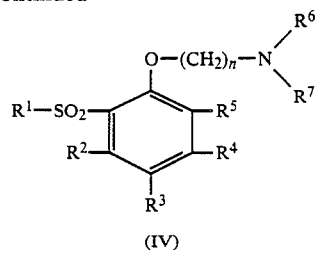

(IV)

In the above formula, $R^1$–$R^7$ are as defined above with respect to the general formula (I), n is 5 or 6 and Hal stands for a halogen atom.

In the above reaction, the amine is usually used in an amount at least equimolar to the ω-halogenoalkoxy derivative.

Although the reaction proceeds without a solvent, solvents inert to the reaction that may be used include an ether, e.g., dioxane, tetrahydrofuran, etc , an amide, e.g. dimethylformamide, N-methylpyrrolidine, etc., an alcohol, e.g., methanol, ethanol, etc , a sulfoxide, e.g., dimethylsulfoxide, etc., or a mixture of any two or more of these.

The reaction temperature is not specifically limited, but usually a temperature between room temperature and 150° C. is employed. A base can be added to the reaction system in order to capture the produced hydrogen chloride and thus promote the reaction. Usable bases are an inorganic base such as sodium hydroxide, potassium hydroxide, sodium carbonate, potassium carbonate; a tertiary amine such as pyridine, triethylamine, etc. The base is usually used in an amount 1–5 times the amount in mole, of the ω-halogenoalkoxy derivative (II) used.

The object compound of this invention, ω-aminoalkoxy derivative (IV) can be obtained either in the form of a free base or in the form of an acid addition salt in accordance with reaction condition. In order to obtain a desired acid addition salt, an ω-aminoalkoxy derivative (IV) may be isolated as the free base and then contacted with a desired acid.

The object compound, ω-aminoalkoxy derivative (IV), either in the form of a free base or in the form of an acid addition salt, can be purified by a conventional method such as recrystallization.

The starting material for the above reaction, that is, an ω-halogenoalkoxy derivative (II) can be obtained by reacting a phenol derivative representd by the general formula (V)

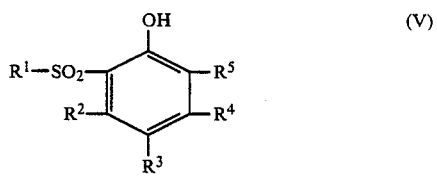

(V)

wherein $R^1$–$R^5$ are as defined with respect to the general formula (I), with a 1,5-dihalogenopentane or 1,6-dihalogenohexane in the presence of alkali.

The ω-halogenoalkoxy derivative (II) can be obtained by reacting a phenol derivative (V) with no less than an equimolar amount of dihalogenoalkane without solvent or in an inert solvent such as benzene, toluene, etc., in the presence of an aqueous solution of a 1–1.5 equivalent of sodium hydroxide and a catalytic amount of a quaternary ammonium salt such as tetrabutylammonium bromide, at a temperature of 25°–100° C. Also the ω-halogenoalkoxy derivative (II) can be obtained by reacting a phenol derivative (V) with not less than an equimolar amount of dihalogenoalkane in an inert solvent such as an amide, e.g., dimethylformamide, N-methylpyrrolidone, etc., an ether, e.g., dioxane, tetrahydrofuran, etc., an aromatic hydrocarbon, e.g., benzene, toluene, etc., in the presence of 1–1.5 equivalents of a metal hydride such as sodium hydride, etc., at a temperature of 0°–100° C.

The above described phenol derivative (V), a starting material, for the above reaction can be obtained by the following reactions:

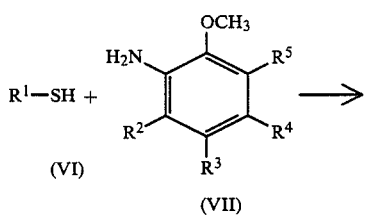

(1)

(VI)  (VII)

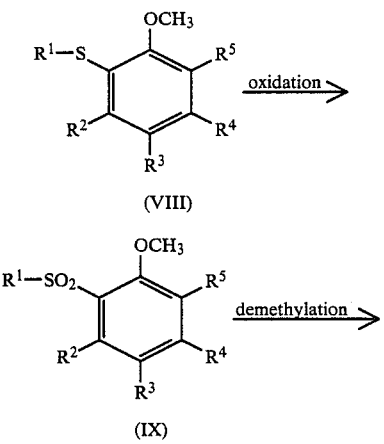

(VIII)

oxidation →

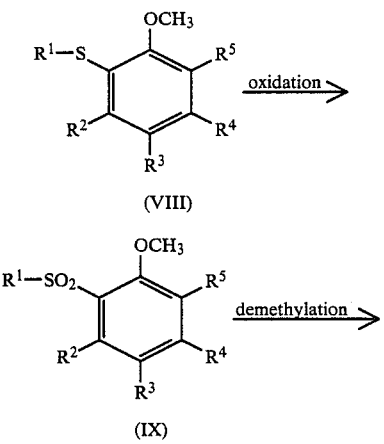

(IX)

demethylation →

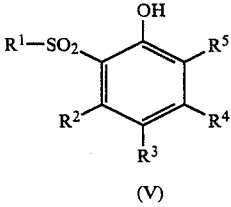

(V)

In the above chemical formulas, $R^1$–$R^5$ are as defined above with respect to the general formula (I).

This reaction scheme can be advantageously employed when $R^1$ is a phenyl substituted with methyl or nitro; phenyl or cyclohexyl; $R^2$–$R^5$ are hydrogen atoms or $R^2$ and $R^5$ are hydrogen atoms and $R^3$ and $R^4$ are halogen atoms.

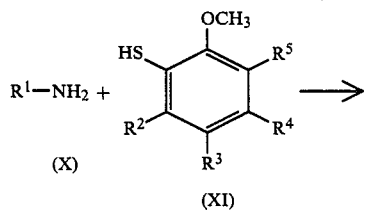

(2)

(X)  (XI)

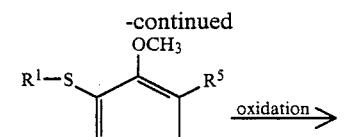

(VIII)

oxidation →

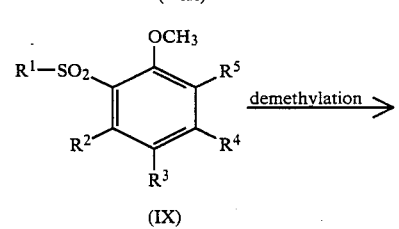

(IX)

demethylation →

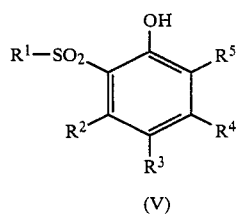

(V)

In the above chemical formulas, $R^1$–$R^5$ are as defined above with respect to the general formula (I).

This reaction scheme can be advantageously employed when $R^1$ is methyl, a phenyl substituted with chlorine atom or nitro or phenyl, and $R^2$–$R^5$ are hydrogen atoms.

The sulfide represented by the above general formula (VIII) can be obtained by reacting a thiophenol represented by the above general formula (VI) with an aniline represented by the general formula (VII) in the reaction scheme (1); and by reacting a thiophenol represented by the general formula (XI) with an aniline represented by the general formula (X) by a conventional method in the reaction scheme (2).

That is, added to an aniline (VII) or (X) are a 3~10-fold (by weight) amount of water and 1.1–3 equivalents of concentrated hydrochloric acid or sulfuric acid, and the aniline is diazotized with an aqueous solution of 1–2 equivalents of nitrous acid. Thereafter, this reaction mixture is added to a mixture of 1–1.5 equivalents of a thiophenol (VI) or (XI) and an aqueous solution of 1.5–3 equivalents of sodium hydroxide or potassium hydroxide, said mixture being heated at 20°–100° C., preferably 50°–80° C., and thus the sulfide (VIII) is obtained.

The sulfone represented by the general formula (IX) is obtained by oxidizing the sulfide of the general formula (VIII) with a suitable oxidation reagent. The reaction can be conducted by the conventional method as follows:

To the sulfide (VIII), glacial acetic acid and 2 equivalents of hydrogen peroxide (30% solution) are added, and oxidation is conducted at 0° C.–100° C. and thus sulfone (IX) is obtained.

A phenol of the general formula (V) is obtained by demethylation of the sulfone of the general formula (IX).

The reaction is conducted by a conventional procedure as follows: A sulfone (IX) is reacted with 1–2 equivalents of boron trichloride or boron tribromide without solvent or in about a 10-fold (by volume) amount of an inert solvent such as dichloromethane, benzene, etc., at a temperature between −80° C. and the refluxing temperature, preferably −10° C.~25° C., and thus a phenol derivative (V) is obtained. The phenol of the general formula (V) can be obtained by reacting a sulfone (IX) with 1-2 equivalents of aluminum chloride without solvent or in 10-fold (by volume) amount of an inert solvent such as nitrobenzene, etc. at a temperature between 50° C. and the refluxing temperature, preferably 80° C.-140° C.

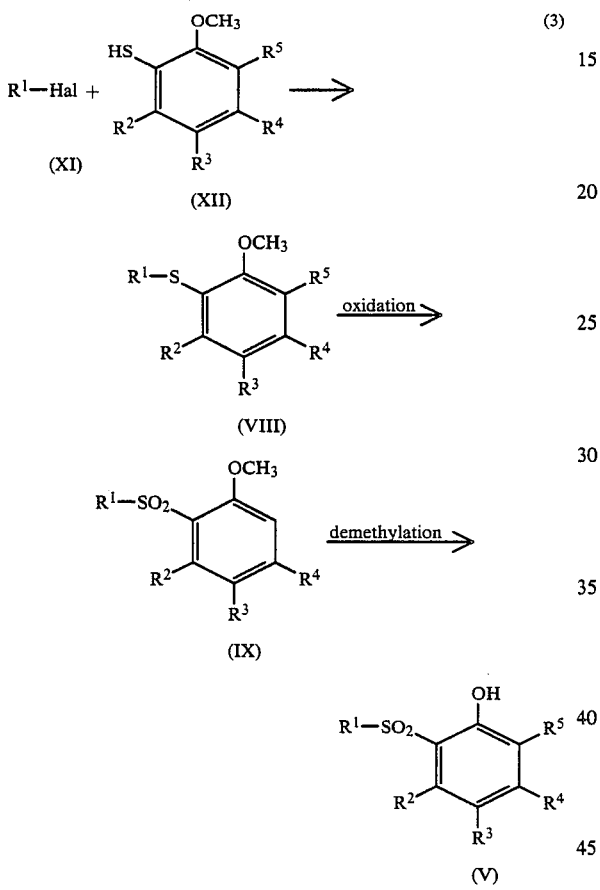

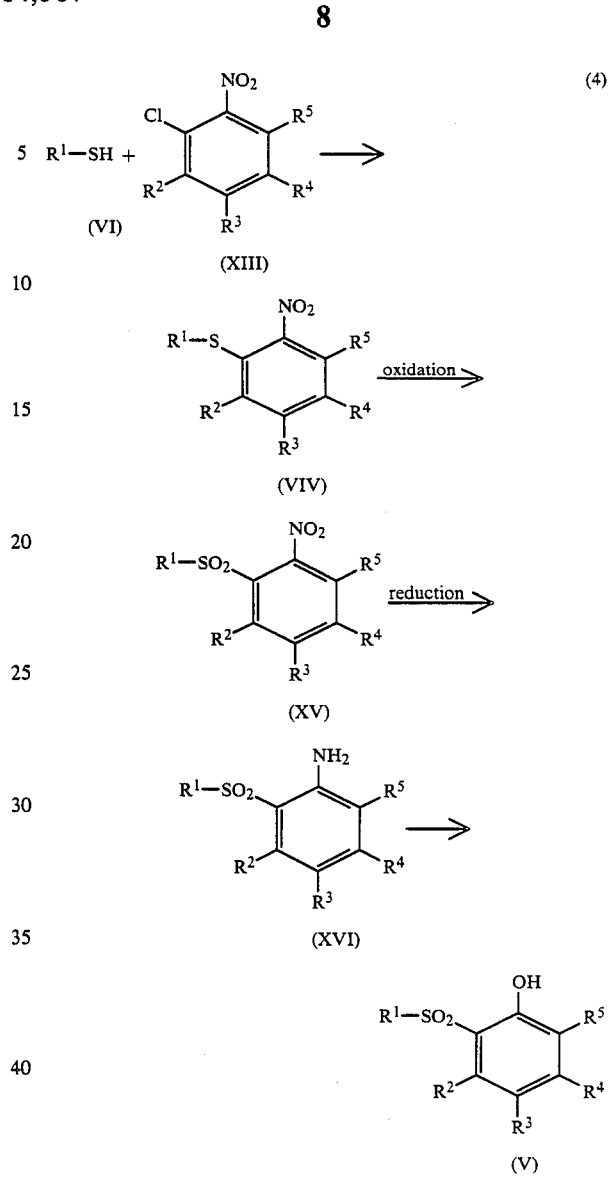

In the above chemical formulas, $R^1$–$R^5$ are as defined above with respect to the general formula (I), and Hal stands for halogen atom.

This reaction scheme is suitable when $R^1$ is a phenyl substituted with nitro or cyclohexyl, and $R^2$–$R^5$ are hydrogen atoms.

The sulfide represented by the general formula (VIII) is obtained by reacting a halide compound represented by the general formula (XI) with a thiophenol represented by the general formula (XII) by a conventional method.

That is, added to a thiophenol (XII) are a 2~10-fold (by volume) amount of a mixed solvent of waer and an alcohol (water:alcohol=2:1 by volume), 1-2 equivalents of sodium hydroxide or potassium hydroxide and 0.9-1.1 equivalents of a halide compound (XI) are added, and the reaction mixture is heated at 30° C.-100° C., preferably 50° C.-80° C. Thus the sulfide (VIII) is obtained. The sulfide (VIII) can be converted in the same manner as in the reaction schemes (1) and (2) to a phonol derivative (V).

In the above chemical formulas, $R^1$–$R^5$ are as defined above with respect to the general formula (I).

These reactions are advantageously employed when $R^1$ is phenyl or a methoxy substituted phenyl.

The sulfide represented by the general formula (XIV) is obtained by reacting a thiophenol (VI) and an o-chloronitrobenzene (XIII) under the same conditions as in the case of the reaction scheme (3). Then, the sulfone (XV) is obtained by oxidizing the sulfide (XIV) under the same condition as in the reaction scheme (1) and (2). Further, the aniline (XVI) is obtained by catalytically reducing the nitro group of the sulfone (XV) by a conventional method.

That is, a sulfone (XV) is catalytically reduced in an ether solvent such as dioxane, tetrahydrofuran, etc. or an alcohol solvent such as methanol, ethanol, etc. in the presence of a reduction catalyst such as 5% palladium-carbon, etc., and an aniline (XVI) is obtained. The reaction is usually carried out in the range of room temperature to 50° C.

Further a phenol derivative (V) is obtained by adding to the aniline (XVI) 1-50 equivalents, preferably 5-10 equivalents of concentrated sulfuric acid without solvent or in about a 5-fold (by volume) amount of water, further adding 1-2 equivalents of sodium nitrite dissolved in a 1.5~2-fold (by volume) amount of water at 0° C.-10° C. and thereafter the mixture is allowed to react at a temperature between 70° C. and the refluxing temperature

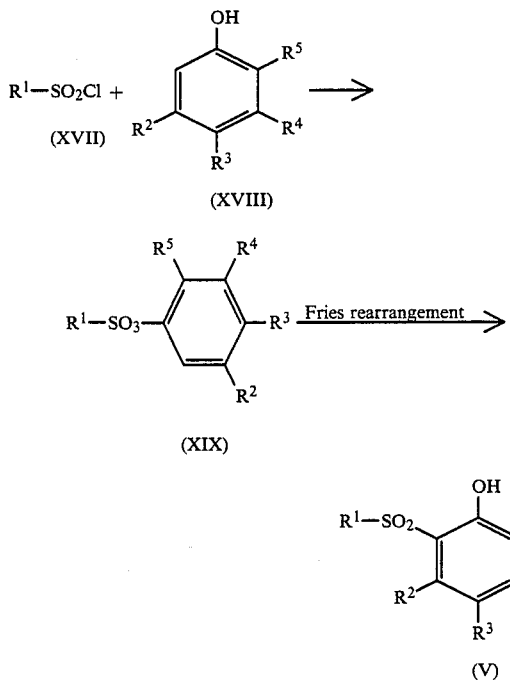

In the above chemical formulas, $R^1$-$R^5$ are as defined above with respect to the general formula (I).

This reaction scheme is suitable when $R^1$ is phenyl or methyl-substituted phenyl, $R^3$ is a chlorine atom, bromine atom or cyano, $R^4$ is a hydrogen or chlorine atom, and $R^2$ and $R^5$ are hydrogen atoms.

In the above reactions, a sulfonic acid ester (XIX) is obtained by reacting a sulfonylchloride (XVII) and a phenol (XVIII). The Fries rearrangement of the sulfonic acid ester (XIX) can be conducted by adding 1.5-2 equivalents of aluminum chloride to the sulfonic acid ester without solvent or in a 10-fold (by volume) amount of inert solvent such as nitrobenzene, etc. at a temperature between 80° C. and the refluxing temperature, preferably at 110°–150° C. Thus a phenol derivative (V) is obtained.

When the final product phenol derivative (V) is a compound represented by the formula:

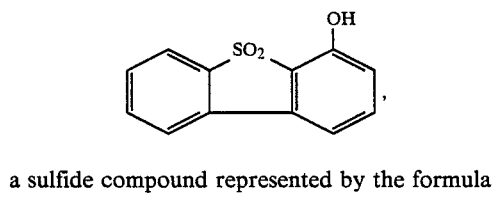

a sulfide compound represented by the formula

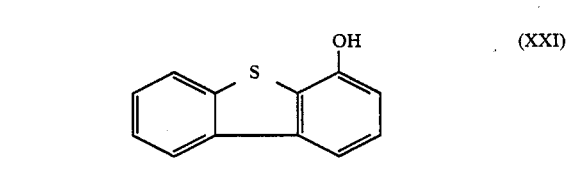

can be oxidized to said phenol derivative (XX) under substantially the same condition as in the oxidation reaction in the reaction scheme (1). The sulfide of the formula (XXI) is known. (Refer to E. Campaigne et al.: J. Heterocyclic Chem., Vol. 7, 753-4 (1969).)

Arylsulfone compounds of the present invention which are represented by the general formula (XXIII) below can be obtained by reacting a halogenomethane derivative represented by the general formula (XXII) below with an amine represented by the general formula (III) below:

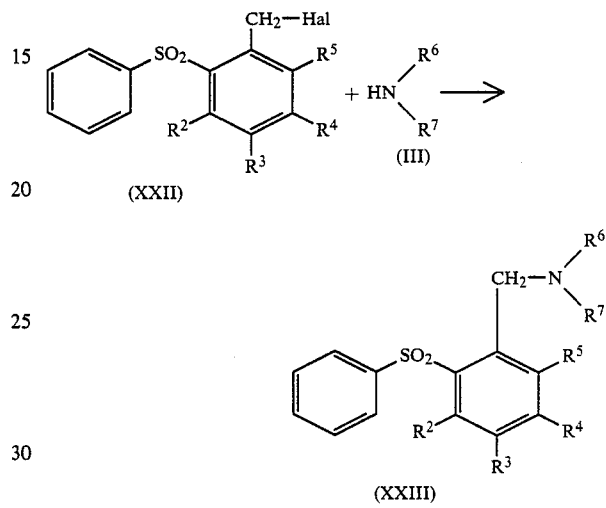

In the above chemical formulas, $R^2$-$R^7$ are as defined above with respect to the general formula (I), and Hal stands for halogen atom.

The reaction conditions are the same as when the arylsulfone compounds of the present invention which are represented by the above general formula (IV) are synthesized from a halogeno derivative and an amine.

The halogenomethane derivative, the starting material of the above described reaction scheme, can be obtained by halogenating 2-methyldiphenylsulfone by a conventional method. That is, 2-methyldiphenylsulfone is reacted with 1-2 equivalents of N-halogenosuccinimide or N-halogenoacetimide in a 1~10-fold (by volume) amount of an inert solvent such as carbon tetrachloride, etc., in the presence of a catalytic amount of benzoyl peroxide, at a temperature between 50° C. and the refluxing temperature, and thus the halogenomethane derivative (XXII) is obtained.

The arylsulfone compound of the present invention which is represented by the general formula (XXVII) below can be obtained by reacting an epoxy derivative represented by the general formula (XXIV) below with an amine represented by the general formula (III) below to form an alcohol derivative represented by the general formula (XXV) and reacting it with an acid anhydride represented by the general formula (XXVI)

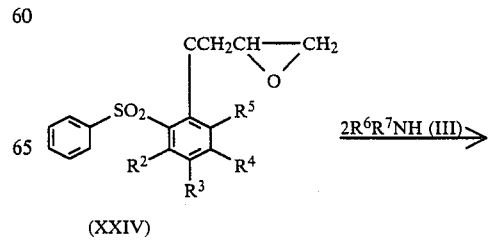

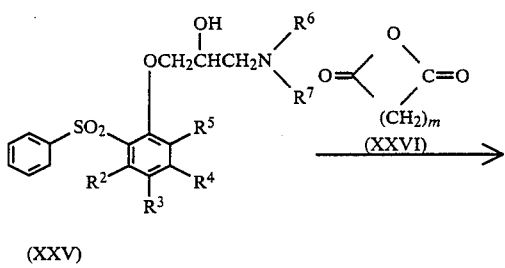

(XXV)

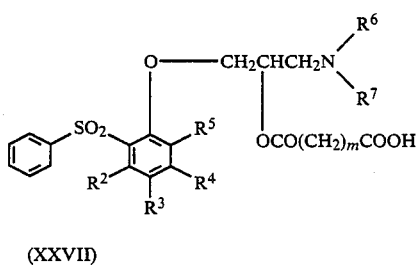

(XXVII)

In the above chemical formulas, $R^2$–$R^7$ and m are as defined above with respect to the general formula (I).

The epoxy derivative represented by the above general formula (XXIV) can be obtained by reacting a 2-hydroxydiphenylsulfone compound with epichlorohydrin in the presence of an alkali.

The arylsulfone compounds and the acid addition salt thereof of the present invention have a stress-ulcer-inhibiting effect. The pharmaceutical effect thereof is explained below with respect to experimental results. The test for stress-ulcer-inhibiting effect was carried out as follows.

Groups (each 5 animals) of non-starved male rats of Douryu strain (available from Shizuoka Laboratory Animal Center, 220-250 g) were each put into a wire net stress cage and were immersed in water of 22°±1° C. to their xiphoid process in order to apply stress to the animals. After 15 hours, the animals were killed and their stomachs were removed. The stomachs were each infused with about 15 ml of 1% formalin and fixed by soaking them in 1% formalin for 10 minutes. The stomachs were then incised along the curvatura ventriculi major and the greatest diameter of any ulcer produced at glandular portions was microscopically measured (×10), the summation of the measured lengths being taken as the ulcer index (mm). Drugs were suspended in a 1% gum arabic solution and orally administered in doses of 2 ml/kg 30 minutes before applying stress. Control groups were given only 1% gum arabic solution and their ulcer indices were compared with those of the groups to which the drugs were administered. The inhibition percentage of each tested drug was calculated. Total administered amount of each tested drug was 50 mg/kg.

The test results are summarized in Table 1. Compound numbers in the table correspond to Example numbers.

TABLE 1

| Tested Compound (Example No.) | Stress Ulcer Inhibition (%) |
|---|---|
| 1 | 73.1 |
| 3 | 78.8 |
| 6 | 41.0 |
| 7 | 40.6 |
| 9 | 42.9 |
| 10 | 50.4 |
| 14 | 48.0 |
| 15 | 41.0 |
| 19 | 66.3 |
| 22 | 51.0 |
| 24 | 63.8 |
| 25 | 73.7 |
| 26 | 46.1 |
| 27 | 85.3 |
| 30 | 53.3 |
| 31 | 60.8 |
| 33 | 48.0 |
| 38 | 54.7 |

As the above experimental results show, the arylsulfone compounds and the acid addition salts thereof of this invention are useful as anti-ulcer agents.

The arylsulfone compounds and the acid addition salts of this invention can be administered in any manner. That is, they can be administered parenterally such as by subcutaneous, intravenous, intramascular or subperitoneal injection or orally.

The dose will depend upon the age of the patient, health condition, body weight, how bad the ulcer is, kind and frequency of simultaneously employed treatment, if any, nature of desired effect, etc.

A normal dose is 0.1–10 mg/kg per day, usually 0.3–5 mg/kg per day, is administered at one time or more.

When the compounds of this invention are orally administered, they are used in the form of a tablet, capsule, powder, liquid, elixir, etc. Parenterally, they are administered in the form of sterilized liquid such as solution or suspension. When they are used thus, a liquid or solid non-toxic vehicle can be used in the formula.

An example of a solid vehicle is a gelatin type capsule. The active ingredient can be tableted or packed together with any adjuvant.

One capsule, tablet or one packet of powder will generally contain 5–95%, preferably 25–90% by weight of the active ingredient. That is, for such modes of administration, it is preferred that 5–500 mg, preferably 5–100 mg of the active ingredient be contained in one dose.

As liquid vehicles, water or an oil derived from a mineral, animal or vegetable source such as paraffin oil, peanut oil, soy bean oil, sesame oil, etc. can be used.

As liquid vehicles, generally physiological salt solution, solutions of dextrose or similar sugars, glycols such as ethylene glycol, propylene glycol, polyethylene glycol, etc. are preferred. When physiological salt solution is used, usually 0.5–20%, preferably 1–10% by weight of the active ingredient is contained.

In the case of liquids for oral administration, a suspension or syrup containing 0.5–10% by weight of the active ingredient is used. In this case, liquid materials such as syrup, pharmaceutical micelles, etc. can be used as vehicles.

DESCRIPTION OF PREPARATION EXAMPLES

Now the invention will be specifically described by way of examples. This invention is not limited by these examples.

EXAMPLE 1

5-[2-(phenylsulfonyl)phenoxy]-N-methylpentylamine hydrochloric acid salt

2-Hydroxydiphenylsulfone (23.4 g) is dissolved in 100 ml of toluene and is mixed with 4.5 g of sodium hydroxide dissolved in 40 ml of water, 82 ml of 1,5-dibromopentane and 1.6 g of tetrabutylammonium bromide, and the mixture is stirred at 60° C. for 3 hours. After cooling, the residue is removed by filtration and the organic layer is separated, washed with water, dried over anhydrous sodium sulfate, evaporated under reduced pressure. Eighty (80) g of methanol is added to the obtained syrup. The deposited crystals are collected by filtration and dried, thus a bromo derivative (32.1 g) having a melting point of 93°-94° C. is obtained.

Three (3.0) g of this bromo derivative is dissolved in 10 ml of tetrahydrofuran, 5.5 ml of a 40% aqueous solution of monomethylamine is added to the solution, and the solution is allowed to stand overnight at room temperature. The solution is then concentrated under reduced pressure, the oily residue is dissolved in ethyl acetate and saturated solution of sodium hydrogen carbonate is added to the solution, and the organic layer is then collected. The organic layer is washed with saturated salt water, dried over anhydrous sodium sulfate, evaporated under reduced pressure to dryness. The residue is chromatographed on a column of silica gel.

The obtained syrup is dissolved in 10 ml of ethanol, and 0.9 ml of a 30% hydrochloric acid-ethanol mixture is added to the solution. The deposited crystals are collected by filtration, dried and thus 2.2 g of 5-[2-(phenylsulfonyl)phenoxy-N-methylpentylamine hydrochloric acid salt having a melting point of 146°-147° C. is obtained.

Also, 3.0 g of the above bromo derivative is mixed with 6 ml of tetrahydrofuran, 2.2 ml of triethylamine and 1.9 g of N-methylbenzylamine, and the mixture is stirred under refluxing for 3 hours.

After cooling, the deposited crystals are removed by filtration and the filtrate is evaporated under reduced pressure to dryness. To the residue are added ethyl acetate and 2N aqueous solution of sodium hydroxide, and the ethyl acetate layer is collected. The ethyl acetate layer is washed with saturated salt solution, dried over anhydrous sodium sulfate and 3.1 ml of a 20% hydrochloric acid-ethyl acetate mixture under ice-chilled condition. The deposited crystals are collected by filtration, recrystallized from isopropyl alcohol and thus 3.3 g of 5-[2-(phenylsulfonyl)phenoxy]-N-benzyl-N-methylpentylamine monohydrochloride having a melting point of 165°-167° C. is obtained.

To the thus obtained benzyl derivative monohydrochloride (3.3 g), 20 ml of methanol, 5 ml of water, 0.5 g of 5%-palladium-carbon are added, and reduction with hydrogen is conducted under atmospheric pressure with agitation at 50° C. for 5 hours. After cooling, the catalyst is removed by filtration and the filtrate is evaporated under reduced pressure to dryness. The residue is crystallized from ethanol and thus 2.3 g of 5-[2-(phenylsulfonyl)phenoxy]-N-methylpentylamine hydrochloric acid salt having a melting point of 146°-147° C. is obtained.

In the same manner as in Example 1, the following compounds are prepared.

| Ex. No. | Compound | m.p. |
| --- | --- | --- |
| 2 | 1-[5-(2-(phenylsulfonyl)phenoxy)pentyl]-4-phenylpiperazine.2HCl | 187-189° C. |
| 3 | 5-[2-(phenylsulfonyl)phenoxy]-N,N—dimethylpentylamine.HCl | 190-191° C. |
| 4 | 5-[2-(phenylsulfonyl)phenoxy]-N—ethylpentylamine.HCl | 173-175° C. |
| 5 | 5-[2-(phenylsulfonyl)phenoxy]-pentylamine.HCl | 153-157° C. |
| 6 | 6-[2-(phenylsulfonyl)phenoxy]-N—methylhexylamine.HCl | 140-141° C. |
| 7 | 6-[2-(phenylsulfonyl)phenoxy]-N,N—dimethylhexylamine.HCl | 202-204° C. |
| 8 | 1-[6-(2-phenylsulfonyl)phenoxy)hexyl]-4-phenylpiperazine.2HCl | 201-204° C. |

EXAMPLE 9

5-[2-(2-methylphenylsulfonyl)phenoxy]-N-methylpentylamine hydrochloric acid salt To 11.8 g of o-anisidine, 17 ml of concentrated hydrochloric acid and 60 ml of water are added, and then 6.6 g of sodium nitrite dissolved in 30 ml of water is added thereto under ice-chilled condition over a 1 hour period. The solution is then added dropwise to a solution of 10.8 g of o-thiocresol and 6.7 g of sodium hydroxide in 45 ml of water at 70° C. over a 4 hour period under agitation. The solution is further stirred at 100° C. for 1 hour. After cooling, benzene extraction is carried out and the benzene layer is washed with water and the benzene is distilled away. The brown oily substance obtained is distilled under reduced pressure and 11.9 g of a sulfide derivative having a boiling point of 142°-145° C./1 mmHg is obtained.

To the thus obtained sulfide derivative (11.9 g), are added 20 ml of acetic acid, 15 ml of 30% hydrogen peroxide solution, and the mixture is stirred at 70° C. for 5 hours for reaction. After reaction, 20 ml of water is added to the mixture, which is cooled, and the deposited crystals are collected by filtration, washed with water, dried and 12.2 g of a sulfone derivative having a melting point of 147°-148° C. is obtained.

The thus obtained sulfone derivative (12.2 g) is dissolved in 60 ml of dichloromethane, and 5.7 ml of boron tribromide dissolved in 15 ml of dichloromethane is added dropwise to the solution under ice-chilled condition. After the solution is stirred for 1 hour under ice-chilled condition, water is added thereto, and the deposited precipitate is removed by filtration. The filtrate is washed, dried over anhydrous sodium sulfate, and the solvent is distilled off, and thus 10.7 g of a phenol derivative having a melting point of 124°-125° C. is obtained.

From this phenol derivative (10.7 g), 10.0 g of 5-[2-(2-methylphenylsulfonyl)phenoxy]-N-methylpentylamine hydrochloric acid salt having a melting point of 167°-168° C. is obtained in the same manner as in Example 1.

In the same manner as in Example 9, the following compounds are prepared.

| Ex. No. | Compound | m.p. |
| --- | --- | --- |
| 10 | 5-[2-(2-methylphenylsulfonyl)phenoxy]-N,N—dimethylpentylamine.HCl | 183-184° C. |
| 11 | 5-[2-(3-nitrophenylsulfonyl)phenoxy]-N—methylpentylamine.HCl | 147-148° C. |
| 12 | 5-[2-(4-chlorophenylsulfonyl)phenoxy]- | 154-156° C. |

-continued

| Ex. No. | Compound | m.p. |
|---|---|---|
| | N—methylpentylamine.HCl | |
| 13 | 5-[2-(4-chlorophenylsulfonyl)phenoxy]-N,N—dimethylpentylamine.HCl | 181–183° C. |

EXAMPLE 14

5-[2-(2-nitrophenylsulfonyl)phenoxy]-N-methylpentylamine hydrochloric acid salt

To 10 g of o-methoxybenzenethiol, are added 3 g of sodium hydroxide and 50 ml of water and 13.1 g of o-bromonitrobenzene dissolved in 20 ml of hot ethanol is added to the mixture at 60° C. over a 10 minute period. The mixture is then stirred under refluxing for 2 hours. After cooled, the deposited crystals are collected by filtration, washed with water, dried, recrystallized from ethanol, and thus 15.3 g of a sulfide derivative having a melting point of 122°–123° C. is obtained. Then, to this sulfide derivative (15.3 g), are added 30 ml of acetic acid, 13 ml of 30% hydrogen peroxide solution and the mixture is stirred at 90° C. for 4 hours. To this reaction mixture is added 30 ml of water and the mixture is cooled. The deposited crystals are collected by filtration, washed with water and dried, and thus 15.6 g of a sulfone derivative having a melting point of 157°–158° C. is obtained. To this sulfone derivative (15.6 g), is added 200 ml of benzene and 10.9 g of aluminum chloride is then added under agitation in a nitrogen atmosphere. The mixture is further stirred under refluxing for 4 hours. After cooling, water is added to the reaction mixture, and the organic layer is collected, washed with water, and extracted with Claisen's alkali (a mixture of 60 ml water, 180 ml methanol and 15 g potassium hydroxide). The resulting oily substance is chromatographed, and 11.6 g of a phenol derivative is obtained as an oily substance.

From this phenol derivative (11.6 g), 9.7 g of 5-[2-(2-nitrophenylsulfonyl)phenoxy]-N-methylpentylamine hydrochloric acid salt having a melting point of 161°–163° C. is obtained in the same manner as in Example 1.

In the same manner as in Example 14, the compound of the following Example 15 is prepared.

EXAMPLE 15

5-[2-(4-nitrophenylsulfonyl)phenoxy]-N-methylpentylamine hydrochloric acid salt.

m.p. 117°–118° C.

EXAMPLE 16

5-[2-(4-methoxyphenylsulfonyl)phenoxy]-N-methylpentylamine hydrochloric acid salt To 3 g of p-methoxybenzenethiol, are added 8.6 g of sodium hydroxide, 10 ml of water and 3.1 g of o-chloronitrobenzene dissolved in 15 ml of warm ethanol is added at 60° C. under agitation over a 10 minute period The mixture is further stirred under refluxing for 2 hours. To the reaction mixture, is added 20 ml of water and the mixture is cooled. The deposited crystals are collected by filtration, washed with water, dried, and thus 5.2 g of a sulfide derivative having a melting pgint of 91°–93° C. is obtained. To the thus obtained sulfide derivative (5.2 g) are added 15 ml of acetic acid and 4.4 ml of 30% hydrogen peroxide are added and the mixture is stirred at 70° C. for 5 hours. To this reaction mixture, 30 ml of water is added and the mixture is cooled. The deposited crystals are collected by filtration, washed with water, dried, and thus 5.5 g of a sulfone derivative having a melting point of 151°–153° C. is obtained. To the thus obtained sulfone derivative (5.5 g) are added 50 ml of tetrahydrofuran and 1 g of 5% palladium carbon, and reduction with hydrogen is conducted at 40° C. under atmospheric pressure for 10 hours. After cooling, the catalyst is removed by filtration, the filtrate is evaporated under reduced pressure to dryness, and 4.8 g of an aniline derivative having a melting point of 124°–126° C. is obtained. To the thus obtained aniline derivative (4.8 g), is added a mixture of 19 ml of water and 14 ml of concentrated sulfuric acid, and 1.3 g of sodium nitrite dissolved in 30 ml of water is added under agitation in an ice-chilled state over a 30-minute period. Agitation is continued in that state for further 30 minutes, and then at 80° C. for 1 hour, and finally at 100° C. for 1 hour. The reaction mixture is subjected to the conventional after-treatment and the Claisen alkali treatment, and 3.8 g of a phenol derivative having a melting point of 121°–122° C. is obtained.

From the thus obtained phenol derivative (3.8 g), 3.6 g of 5-[2-(4-methoxyphenylsulfonyl)phenoxy]-N-methylpentylamine hydrochloric acid salt having a melting point of 167°–168° C. is obtained.

In the same manner as in Example 16, the following compound of Example 17 is prepared.

EXAMPLE 17

5-[2-(4-methoxyphenylsulfonyl)phenoxy]-N,N-dimethylpentylamine hydrochloric acid salt m.p. 182°–183° C.

EXAMPLE 18

5-[4-cyano-2-(phenylsulfonyl)phenoxy]-N-methylpentylamine hydrochloric acid salt p-Cyanophenol (29.6 g) is dissolved in 230 ml of acetone, 10.7 g of sodium hydroxide dissolved in 100 ml of water is dropwise added thereto under agitation in ice-chilled state, and further 46.1 g of benzenesulfonic acid chloride is added dropwise over a 30-minute period. After agitation is continued for another 1 hour, the organic layer is collected and washed with saturated salt solution and a small amount of hydrochloric acid and the acetone is distilled off under reduced pressure. The obtained oily substance is dissolved in chloroform, washed with water, dried over anhydrous sodium sulfate, and thus 64.6 g of sulfonic acid ester is obtained.

Thirty (30) g of the obtained sulfonic acid ester is dissolved in 300 ml of nitrobenzene, and 30.9 g of aluminum chloride is added. The mixture is stirred at 120° C. in a nitrogen atmosphere for 20 hours. After cooling, the reaction mixture is poured into water, and the organic layer is collected, washed with water, and extracted with Claisen's alkali. The alkaline layer is collected and is stirred under ice-chilled condition for 1 hour, and the deposited crystals are collected. The collected crystals are suspended in ethyl acetate and stirred under ice-chilled condition, and thereafter the mixture is acidified with 6N hydrochloric acid. The organic layer is collected, washed with saturated salt solution, dried over anhydrous sodium sulfate. The ethyl acetate is distilled off under reduced pressure, the residue is dried, and thus 19.0 g of a phenol derivative having a melting point of 143°–145° C.

The thus obtained phenol derivative (19.0 g) is dissolved in 60 ml of dried dimethylformamide, and the solution is slowly added dropwise to a suspension of 3.7 g of sodium hydride (50% dispersion in mineral oil) in 30 ml of dried dimethylformamide under agitation in a water-cooled state. After the addition is finished, the mixture is stirred at 50° C. for 30 minutes, 46 ml of 1,5-dibromopentane is added and the mixture is stirred at 50° C. for 2 hours. After cooling, the reaction mixture is poured into water, and the organic layer is extracted with chloroform, washed with water, and dried over anhydrous sodium sulfate. The solvent is distilled off under reduced pressure, and the residue is chromatographed with a column of silica gel. Thus 22.5 g of a bromo derivative having a melting point of 161°–162° C. is obtained.

Ten (10) g of the thus obtained bromo derivative is dissolved in 100 ml of tetrahydrofuran, and 40 ml of 40% aqueous solution of monomethylamine is added. The mixture is allowed to stand overnight. Thereafter, the reaction mixture is concentrated under reduced pressure, and a saturated aqueous solution of sodium hydrogen carbonate is added thereto. The organic layer is collected and washed with saturated salt solution, dried over anhydrous sodium sulfate, and 5 ml of a 20%-hydrogen chloride-ethyl acetate mixture is added thereto under agitation in water-cooled state. The deposited crystals are collected by filtration and recrystallized from ethanol and thus 7.7 g of 5-[4-cyano-2-(phenylsulfonyl)phenoxy]-N-methylpentylamine hydrochloric acid salt having a melting point of 179°–181° C. is obtained.

In the same manner as in Example 18, the following compounds are prepared.

| Ex. No. | Compound | m.p. |
| --- | --- | --- |
| 19 | 5-[4-bromo-2-(phenylsulfonyl)phenoxy]-N-methylpentylamine.HCl | 191–192° C. |
| 20 | 5-[3,4-dichloro-2-(phenylsulfonyl)phenoxy]-N-methylpentylamine.HCl | 152–154° C. |
| 21 | 5-[3,4-dichloro-2-(phenylsulfonyl)phenoxy]-N,N—dimethylpentylamine.HCl | 175–178° C. |

EXAMPLE 22

5-[4-carboxy-2-(phenylsulfonyl)phenoxy]-N-methylpentylamine hydrochloric acid salt To 5.0 g of the 5-[4-cyano-2-(phenylsulfonyl)phenoxy]-N-methylpentylamine hydrochloric acid salt obtained in Example 5, 70 ml of 6N hydrochloric acid is added and the mixture is stirred under a nitrogen atmosphere at 100° C. for 15 hours. After cooling, the deposited crystals are collected by filtration, and recrystallized from an ethanol-water mixture, and 4.5 g of 5-[4-carboxy-2-(phenylsulfonyl)phenoxy]-N-methylpentylamine hydrochloric acid salt having a melting point of 224°–226° C. is obtained.

In the same manner as in Example 22, the following compound of Example 23 is obtained.

EXAMPLE 23

5-[4-carboxy-2-(phenylsulfonyl)phenoxy]-N,N-dimethylpentylamine hydrochloric acid salt m.p. 212°–215° C.

EXAMPLE 24

2-(3-carboxypropionyloxy)-3-2-(phenylsulfonyl)phenoxy]-N,N-dimethylpropylamine hydrochloric acid salt A solution of 10.0 g of o-hydroxydiphenylsulfone in 30 ml of dried dimethylformamide is added slowly dropwise into a suspension of 2.2 g of sodium hydride (50% dispersion in mineral oil) in 20 ml dried dimethylformamide under agitation in a water-cooled state. After addition is finished, the mixture is stirred at 50° C. for 30 minutes, 16 ml of epichlorohydrin is added thereto and the mixture is stirred at 50° C. for 2 hours. After cooling, water and ethyl acetate are added to the reaction mixture. The organic phase is collected, washed with saturated salt solution, dried over anhydrous sodium sulfate, and the solvent is distilled off under reduced pressure. To the residue, n-hexane is added, and the solid material is triturated and collected by filtration, dried, and thus 11.8 g of an epoxy derivative having a melting point of 106°–109° C. is obtained.

The thus obtained epoxy derivative (11.8 g) is dissolved in 80 ml of tetrahydrofuran, 43 ml of 50% aqueous solution of dimethylamine is added to the solution, and the reaction mixture is allowed to stand overnight at room temperature. The reaction mixture is then concentrated under reduced pressure, and the deposited oily substance is dissolved in ethyl acetate. The organic phase is collected, washed with saturated salt solution, dried over anhydrous sodium sulfate, and 7.7 ml of 20% hydrogen chloride-ethyl acetate solution is added thereto. The deposited crystals are collected by filtration and recrystallized from isopropyl alcohol, and thus 11.9 g of 1-dimethylamino-3-[2-(phenylsulfonyl)phenoxy]-2-propanol hydrochloric acid salt having a melting point of 159°–161° C. is obtained. Then, 2.3 g of the thus obtained hydrochloric acid salt is dehydrochlorinated by a conventional method and 2.0 g of an oily substance is obtained. To this, 10 ml of tetrahydrofuran and 0.8 g of succinic acid anhydride are added and the mixture is stirred under refluxing for 3 hours. Thereafter, the solvent is distilled off under reduced pressure. The residue is dissolved in chloroform, and 20% hydrogen chloride-ethyl acetate mixture is added thereto under agitation in the ice-chilled state. Ether is added to the mixture and the deposited crystals are collected by filtration. The collected crystals are suspended in acetone, and the suspension is stirred under refluxing for 30 minutes. After cooled, the crystals are collected by filtration, dried and thus 2.2 g of 2-(3-carboxypropionyloxy)-3-[2-(phenylsulfonyl)phenoxy]-N,N-dimethylpropionylamine hydrochloric acid having a melting point of 116°–117° C. is obtained.

EXAMPLE 25

5-[2-(cyclohexylsulfonyl)phenoxy]-N-methylpentylamine hydrochloric acid salt

Fourteen (14) g of o-methoxybenzenethiol is slowly dropwise added to a suspension of 5.0 g of sodium hydride (50% dispersion in mineral oil) in 70 ml of dried dimethylformamide under agitation in the water-cooled state. After addition is finished, agitation is continued for 30 minutes at room temperature, and then 17.9 g of cyclohexyl bromide is added to the mixture and it is stirred at room temperature for 3 hours. Water and ethyl acetate are then added to the reaction mixture and the organic phase is collected. The collected organic phase is washed with saturated salt solution, dried over anhydrous sodium sulfate, the solvent is distilled off under reduced pressure and thus 14.6 g of a sulfide derivative is obtained as an oily substance.

The thus obtained sulfide derivative (14.6 g) is dissolved in 70 ml of dichloromethane, and the solution is stirred at −10° C., and 7.4 ml of boron tribromide dissolved in 20 ml of dichloromethane is added dropwise thereto. After addition is finished, the mixture is stirred in an ice-chilled state for 1 hour. Water is then added, the deposited precipitate is removed by filtration, the filtrate is washed with water, dried over anhydrous sodium sulfate, the solvent is distilled off, and thus 10.9 g of a phenol derivative is obtained as an oil substance.

The thus obtained phenol derivative (10 9 g) is dissolved in 50 ml of benzene, to which 55 ml of 1N sodium hydroxide aqueous solution, 0.9 g of tetra-n-butylammonium bromide and 35 ml of 1,5-dibromopentane are added, and the mixture is stirred under refluxing for 2 hours. After cooling, the organic phase is collected, washed with water, dried over anhydrous sodium sulfate, and the solvent is distilled off. The residue is chromatographed and 16.1 g of a bromosulfide derivative is obtained as an oily substance.

This bromosulfide derivative (16.1 g) is dissolved in 90 ml of chloroform, and 20.3 g of 80% m-chloroperbenzoic acid is slowly added to the solution under agitation in the water-cooled state. Thereafter, the solution is stirred at room temperature for 1 hour, the deposited crystals are removed by filtration, and the filtrate is washed with saturated sodium sulfite aqueous solution, then with saturated salt solution, and dried over anhydrous sodium sulfate. The solvent is distilled off and thus 13.3 g of a bromosulfone derivative is obtained as an oily substance.

From 2 g of this bromosulfone derivative, 1.5 g of 5-[2-(cyclohexylsulfonyl)phenoxy]-N-methylpentylamine hydrochloric acid salt having a melting point of 103°–105° C. is obtained in the same manner as in Example 1.

In the same manner as in Example 25, the compound of the following Example 26 is obtained.

EXAMPLE 26

5-[2-(cyclohexylsulfonyl)phenoxy]-N,N-dimethylpentylamine hydrochloric acid salt.

m.p. 132°–135° C.

EXAMPLE 27

N-[2-(phenylsulfonyl)benzyl]-N-methylamine hydrochloric acid salt

To 50 g of o-methylbiphenylsulfone, which has been prepared in the same manner as in Example 9, 250 ml of carbon tetrachloride, 90 g of N-bromosuccinimide and 0.5 g of benzoyl peroxide are added, and the mixture is stirred under refluxing for 20 hours. After cooling, the deposited crystals are removed by filtration, the filtrate is washed with water, dried over anhydrous sodium sulfate, the solvent is distilled off, and thus 74.3 g of a bromo derivative is obtained as an oily substance.

From 5.0 g of this bromo derivative, 2.1 g of N-[2-(phenylsulfonyl)benzyl]-N-methylamine hydrochloride having a melting point of 181°–182° C. is obtained.

In the same manner as in Example 27, the following compounds are prepared.

| Ex. No. | Compounds | m.p. |
|---|---|---|
| 28 | N—[2-(phenylsulfonyl)benzyl]-N,N—dimethylamine.HCl | 185–187° C. |
| 29 | N—[2-(phenylsulfonyl)benzyl]-N—ethylamine.HCl | 168–170° C. |
| 30 | N'—[2-(phenylsulfonyl)benzyl]-N,N—dimethylethylenediamine.2HCl | 187–190° C. |
| 31 | N'—methyl-N'—[2-(phenylsulfonyl)benzyl]-N—methylethylenediamine.2HCl | 161–165° C. |
| 32 | 1-[2-(phenylsulfonyl)benzyl]-piperazine.2HCl | 157–161° C. |
| 33 | 1-[2-(phenylsulfonyl)benzyl]-4-methyl-piperazine.2HCl | 164–167° C. |
| 34 | 1-[2-(phenylsulfonyl)benzyl]-4-(2-hydroxyethyl)piperazine.2HCl | 192–194° C. |
| 35 | 1-[2-(phenylsulfonyl)benzyl]-4-phenylpiperazine.2HCl | 140–143° C. |
| 36 | N—[2-(2-methoxyphenylsulfonyl)benzyl]-N—methylamine.HCl | 153–156° C. |
| 37 | 1-[2-(2-methoxyphenylsulfonyl)benzyl]-4-methylpiperazine.2HCl | 193–198° C. |

EXAMPLE 38

4-(5-dimethylaminopentyloxy)dibenzothiophene-5,5-dioxide hydrochloric acid salt

Two (2.0) g of 4-hydroxydibenzothiophene, which has been prepared by a conventional method is oxidized in the same manner as in Example 9, and a sulfone derivative is obtained. From this sulfone derivative, 1.4 g of 4-(5-dimethylaminopentyloxy)dibenzothiophene-5,5-dioxide hydrochloric acid salt having a melting point of 186°–188° C. is obtained in the same manner as in Example 1.

We claim:

1. An arylsulfone compound represented by formula (I):

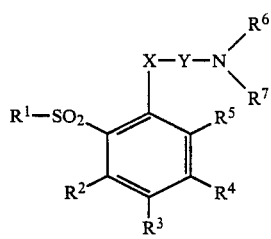

wherein $R^1$ is phenyl; $R^2$ is hydrogen; $R^3$ is hydrogen, halogen, cyano or carboxyl; $R^4$ is hydrogen or halogen; $R^5$ is hydrogen; X is an oxygen atom or a methylene group; Y is —$(CH_2)_n$—, wherein n is zero or 6; and $R^6$ and $R^7$ are each independently a hydrogen atom or a $C_1$-$C_3$ alkyl group; or a pharmaceutically acceptable salt thereof.

2. The arylsulfone compound of claim 1, wherein the salt of said compound is the hydrochloric acid salt, the hydrobromic acid salt, the sulfuric acid salt, the phosphoric acid salt, the nitric acid salt, the acetic acid salt, the succinic acid salt, the adipic acid salt, the propionic acid salt, the tartaric acid salt, the maleic acid salt, the citric acid salt, the benzoic acid salt, the toluenesulfonic acid salt, or the methanesulfonic acid salt.

* * * * *